United States Patent
Creasey et al.

(10) Patent No.: US 7,241,260 B2
(45) Date of Patent: Jul. 10, 2007

(54) SPHINCTERIC CONTROL SYSTEM

(75) Inventors: Graham Creasey, Lane Cove (AU); James Finlay Patrick, Roseville (AU)

(73) Assignee: Neopraxis Pty. Limited, Lane Cove, NSW (AU)

(*) Notice: Subject to any disclaimer, the term of this patent is extended or adjusted under 35 U.S.C. 154(b) by 233 days.

(21) Appl. No.: 10/943,972

(22) Filed: Sep. 20, 2004

(65) Prior Publication Data

US 2005/0192635 A1  Sep. 1, 2005

(30) Foreign Application Priority Data

Sep. 19, 2003  (AU) .............................. 2003905119

(51) Int. Cl.
    *A61F 2/00* (2006.01)
(52) U.S. Cl. .................... 600/29; 128/DIG. 25; 607/41
(58) Field of Classification Search ............ 600/29–32; 128/DIG. 25; 607/1–3, 39–41, 48
    See application file for complete search history.

(56) References Cited

U.S. PATENT DOCUMENTS

2002/0049364 A1* 4/2002 Pregenzer et al. ............ 600/30
2005/0216069 A1* 9/2005 Cohen et al. ................. 607/41
2006/0036293 A1* 2/2006 Whitehurst et al. ........... 607/40
2006/0149333 A1* 7/2006 Tanagho et al. .............. 607/41

FOREIGN PATENT DOCUMENTS

WO  WO 01/10357 A1  2/2001
WO  WO 03/099118 A1  12/2003

* cited by examiner

*Primary Examiner*—John P. Lacyk
(74) *Attorney, Agent, or Firm*—Jagtiani + Guttag

(57) ABSTRACT

A sphincteric control system for controlling the function of a bodily organ, such as the bladder. The system comprises a first implanted sphincter (12) disposed about a portion of the bodily organ, a second implanted sphincter (13) disposed about a portion of the bodily organ, and a stimulator unit (20) that is adapted to apply electrical stimulation to each of the first and second implanted sphincters. One of the first or second implanted sphincters is made from a smooth muscle and the other of the first or second implanted sphincters is made from a striated muscle.

23 Claims, 3 Drawing Sheets

SPHINCTERIC CONTROL SYSTEM

CROSS-REFERENCE TO RELATED APPLICATIONS

This application claims priority from Australian Provisional Patent Application No. 2003905119, entitled "Sphincteric Control System," filed Sep. 19, 2004, which is hereby incorporated by referenced herein in its entirety.

BACKGROUND

Field of the Invention

The present invention relates to a device and method for controlling the function of a bodily organ and in particular, an implantable electrical stimulation device and method for treating urinary incontinence.

In the U.S., it is estimated that bladder control problems affect more than 25 million Americans every year. Problems range from conditions such as bedwetting in children to chronic incontinence in adults. Bladder control problems are far more prevalent in women than men, with 10-30% of women affected in the general population aged 15-64 years old, compared with 1.5-5% of men being affected. It is considered that at least 50% of residents in U.S. nursing homes are affected and of this number, 70% are women.

Urinary incontinence is often the result of anatomic, physiologic, or pathologic (disease) factors. Congenital and acquired disorders of muscle innervation (e.g. ALS, spina bifida, multiple sclerosis) eventually cause inadequate urinary storage or control. Acute and temporary incontinence is commonly caused by childbirth, limited mobility, side effect of medication, or a urinary tract infection. Chronic incontinence is, however, often attributed to the following factors: birth defects, bladder muscle weakness, blocked urethra (due to benign prostrate hyperplasia, tumor, etc.), brain or spinal cord injury, nerve disorders, or pelvic floor muscle weakness.

Of all such conditions, perhaps the most common is stress incontinence which accounts for approximately 60% of all urinary incontinence cases. Stress incontinence occurs when the pelvic floor muscles weaken, allowing the bladder to push against the urethra, damaged urinary sphincters have also been attributed to causing stress incontinence. Typically, urine emission occurs when the abdominal muscles push down on the lower bladder and often common everyday activities and events such as laughing, coughing, sneezing, exercising or lifting objects will cause a slight loss of urine.

It is understood that stress incontinence occurs when the bladder neck and the urethra do not close properly. If these structures move down and bulge (herniate) through weakened pelvic floor muscles, they are said to be hypermobile. Herniation (or cystocele) changes the angle of the urethra, which causes it to remain open and allows urine to flow. Studies have shown that there are three basic classifications of stress incontinence.

The first class, known as TYPE I, is where the bladder neck and urethra are open and slightly hypermobile, and the urethra moves down less than 2 cm when stressed. Patients suffering from this type of stress incontinence have little or no sign of cystocele.

The next class is referred to as TYPE II, and is where the bladder neck and the urethra are closed and hypermobile, and the urethra moves down more than 2 cm when stressed. Patients having cystocele inside the vagina are considered to have TYPE IIA stress incontinence, whilst those having cystocele outside the vagina are classified as having TYPE IIB stress incontinence.

The third class, referred to as TYPE III (severe) is where the urethral sphincter is very weak (called intrinsic sphincter deficiency.)

Urge incontinence is another common condition experienced by those suffering urinary incontinence. In this condition, the sufferer experiences a strong desire to urinate followed by involuntary contractions of the bladder. In this regard, as the bladder contracts, urine is released quickly, making it practically impossible for urge incontinence sufferers to predict when the problem will occur. This condition is often caused by infections, sphincter disorders or nervous system disorders that affect the bladder.

In men, prostrate cancer is often the cause of urge incontinence. In this regard, an enlarged prostate can affect bladder control as the urethra passes through the prostate gland. When enlarged, the prostate can compress the urethra and prevent the normal flow of urine. The brain receives the message to urinate, but the blockage prevents normal urination. This type of incontinence, called urge incontinence, can be treated in a number of ways, including committing to a present bladder-voiding schedule to prevent too much urine from accumulating in the bladder.

In all cases of urinary incontinence, there is a social stigma attached and it is often due to this stigma that many sufferers do not even report the problem to a health care provider. Often, once the condition is reported, many physicians and nurses fail to pursue investigation of the urinary incontinence and merely address the condition through the provision of absorbent underwear and such devices. As a result of this lack of education and understanding, this medical problem is vastly under-diagnosed and under-reported.

Various proposals have been put forward to actually treat the various forms of urinary incontinence. One approach has been to provide a prosthetic sphincter valve to replace or supplement the defective or damaged urethral sphincter. It has also been proposed to provide electrical stimulation to the muscles of the defective sphincter to correct the defect, however, no such proposals have as yet proven ideal in addressing the problem.

More recently, it has been proposed in International Patent Application No. PCT/AU00/00925 to provide an auxiliary sphincter of innervated smooth muscle to be surgically implanted about the urethra to control the flow of urine there-through. This auxiliary sphincter is then stimulated with a low frequency signal causing the sphincter to contract restricting urine flow, and upon receipt of a signal form the patient indicative of the desire to urinate, stimulation is ceased, allowing urine to flow. Whilst such an approach may be useful in treating general incontinence, it is not ideal with regard to the treatment of stress incontinence, particularly in instances where there is a sudden increase in intra-abdominal pressure.

The natural urethral sphincter mechanism in humans utilizes both smooth and striated muscle, with the smooth muscle predominately in the internal sphincter providing long term tone and the striated muscle in the external urethral sphincter contracting briefly and strongly to prevent stress incontinence during sudden increases in intra-abdominal pressure. In this regard, it is considered that an approach that better replicates the natural urethral sphincter mechanism is required to provide a more complete solution to the various types of urinary incontinence.

SUMMARY

According to a first aspect of the invention there is provided a sphincteric control system for controlling the function of a bodily organ, the sphincteric control system comprising:
- a first implanted sphincter disposed about a portion of the bodily organ;
- a second implanted sphincter disposed about a portion of the bodily organ; and
- a stimulator unit adapted to apply electrical stimulation to each of said first and second implanted sphincters;
- wherein one of said first or second implanted sphincters is made from a smooth muscle and the other of said first or second implanted sphincters is made from a striated muscle.

In one embodiment, the stimulator unit can control the bodily organ by delivering a predetermined electrical stimulation signal to each of the implanted sphincters, causing said sphincters to contract and relax about the bodily organ. The predetermined electrical stimulation may be in the form of a low frequency stimulation signal when applied to the smooth muscle sphincter and in the form of a high frequency stimulation signal when applied to the striated muscle sphincter.

In a further embodiment, the stimulator unit can apply the electrical stimulation to each of the implanted sphincters via stimulating electrode elements positioned in or on the implanted sphincters.

According to a second aspect, the present invention is a method of controlling the function of a bodily organ comprising:
- implanting a first sphincter about a portion of the bodily organ;
- implanting a second sphincter about a portion of the bodily organ; and
- applying electrical stimulation to each of said first and second implanted sphincters using a stimulator unit;
- wherein one of said first or second implanted sphincters is made from a smooth muscle and the other of said first or second implanted sphincters is made from a striated muscle.

BRIEF DESCRIPTION OF THE DRAWINGS

By way of example only, preferred embodiments of the invention are now described with reference to the accompanying drawings, in which.

DETAILED DESCRIPTION

Figure 1:
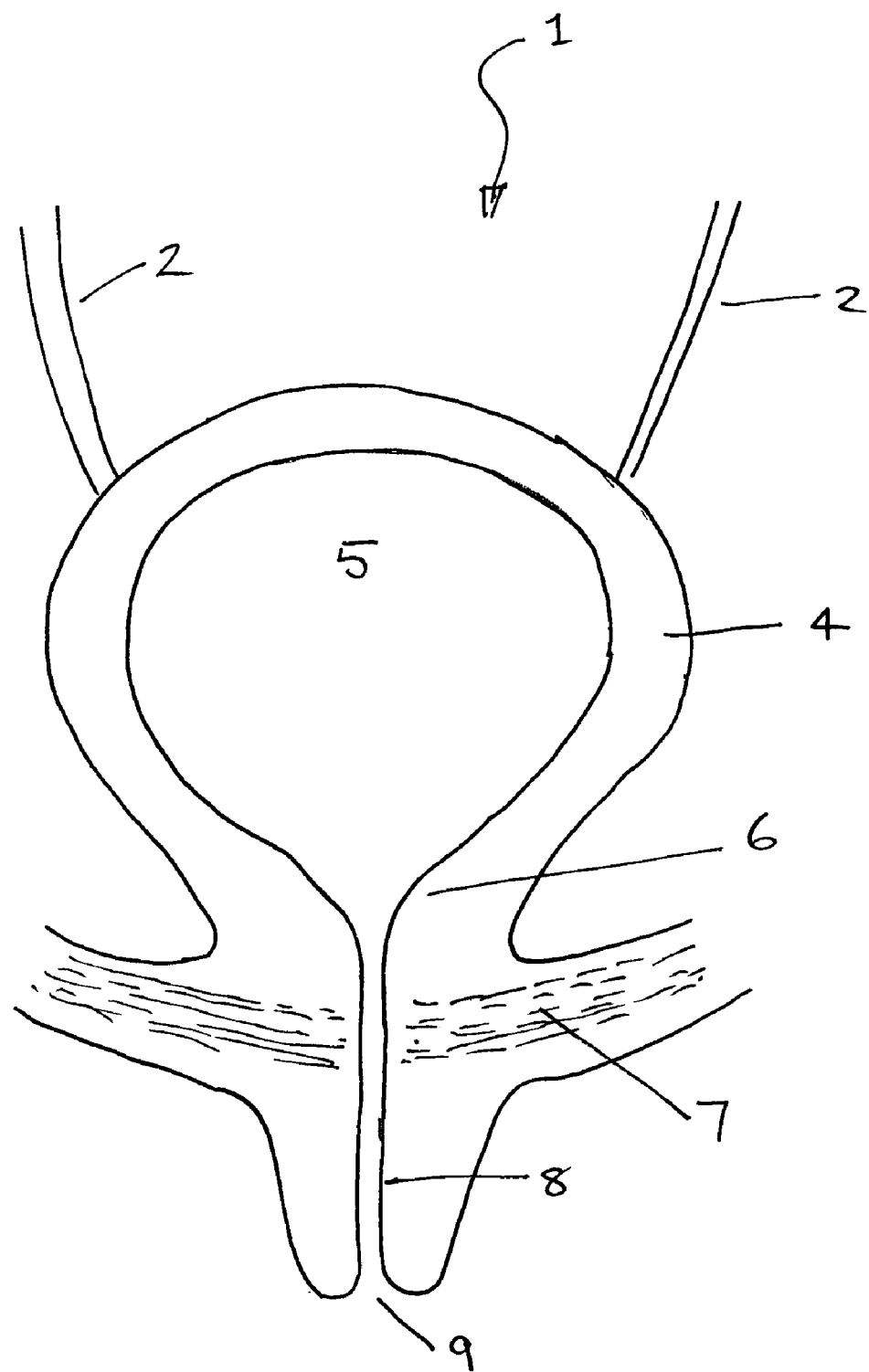
FIG. 1 is a view of the lower urinary tract of a normally functioning female.

In FIG. 1, the reference numeral 1 represents the lower urinary tract of a normally functioning female. The kidneys (not shown) regulate the blood and remove waste from the blood, in the form of urine. In normal humans, the kidneys filter 160 liters of blood a day, and water makes up nearly 95% of the total volume of urine excreted by the kidneys, with the remaining 5% consisting of dissolved solutes, or wastes such as urea, uric acid and creatinine. Urine is steadily excreted from the kidneys and passes through two ureters 2 to the bladder 5 by means of muscle contractions and the force of gravity. Once in the bladder 5, urine is temporarily stored until it is voided from the body through urethra 8.

The bladder 5 consists of a hollow muscular storage organ that is found in the pelvis behind the pelvic bone (pubic symphysis) and a drainage tube, called the urethra 8, that exits the outside of the body. The bladder 5, ureters 2, and urethra 8.

The urinary bladder 5 is an elastic organ that changes shape according to the amount of urine it contains. It resembles a deflated balloon when empty but becomes somewhat pear-shaped and rises into the abdominal cavity when the amount of urine increases.

The bladder wall has three main layers of muscle: the mucosa, submucosa, and detrusor muscle 4. The mucosa is the innermost layer and is composed of transitional cell epithelium. The submucosa lies immediately beneath the mucosa and its basement membrane. It is composed of blood vessels which supply the mucosa with nutrients and the lymph nodes which aid in the removal of waste products. The detrusor muscle 4 is a thick layer of smooth muscle which expands to store urine and contracts to expel urine. The urethra 8 is a small tube which leads from the floor or neck of the urinary bladder to the outside of the body. In women, the urethra 8 is approximately 1.5 inches (or about 3.81 cm) long and is found in the front wall of the vagina. The urethral orifice or meatus 9 is the outside opening of the urethra 8 and is located between the clitoris and the vaginal opening. In men, the urethra 8 is approximately 8 inches (or about 20.32 cm) long. When it leaves the bladder, it passes downward through the prostate gland, the pelvic muscle and finally through the length of the penis until it ends at the urethral orifice or opening at the tip of the glans penis.

Storage and emptying of the bladder are regulated by the internal 6 and external 7 urethral sphincters. Sphincters are made up of a ring-like band of muscle fibers that close off a natural opening in the body. Sphincters are normally in a closed position and need stimulation to open. Continence depends on two factors: normal lower urinary tract support and normal sphincteric function.

Lying below the internal sphincter 6 is the external sphincter 7 which is made up of smooth muscle mixed with striated, or striped, muscle of the pelvic floor or pelvic diaphragm. Unlike the smooth muscles that an individual cannot consciously control, the striated muscles of the external sphincter allow for voluntary interruption of abdominal pressure to prevent urine leakage, such as occurs in coughing or sneezing.

These three sets of muscles must work in close unison to control the various stages of urinary bladder filling and emptying. During the filling stage, only minimal activity is needed to produce closure of the external urethral sphincter 7. At a certain point during bladder filling, the internal pressure within the bladder 5 becomes strong enough to activate stretch receptors in the bladder wall. When these stretch receptors send a message to the nervous system, small contractile waves occur in the detrusor muscle 4 and the internal urethral sphincter 6 automatically relaxes and becomes funnel shaped. The external sphincter 7 must now be consciously tightened, and the urge to urinate becomes very apparent. To urinate, a person must relax the external sphincter 7.

The advantage of this system is that, during the early stages of bladder filling, a person remains unaware of the slowly accumulating urine and is not required to keep the external sphincter tightly closed. This only becomes necessary when enough urine collects to relax the internal sphincter 6.

In operation, the lower urinary tract 1 is essentially a high volume, low pressure system. Even when the bladder 5 is full of urine, the elasticity of the bladder 5 allows room for the additional fluid without causing high pressure within the bladder itself. Normal bladder capacity is somewhere between 400 to 600 cc however, the urinary bladder can normally hold 250 to 350 cc of urine before the urge to void becomes conscious. Urinary continence is maintained as long as the pressure within the urethra 8 (intra-urethral pressure) remains higher than the pressure within the cavity of the bladder 5 (intravesical pressure).

Normally, continence is maintained during increased intra-abdominal pressure (which occurs with coughing, laughing, or sneezing) because urethral pressure rises more than pressure within the bladder cavity as a response to the increased intra-abdominal pressure.

As mentioned above, when approximately 250 to 300 cc of urine is in the bladder, the internal pressure within the bladder becomes strong enough to activate stretch receptors in the bladder wall. When these stretch receptors send a message to the nervous system, small contractile waves occur in the detrusor muscle and the internal urethral sphincter automatically relaxes and becomes funnel shaped. The external sphincter must now be consciously tightened and the urge to urinate becomes very apparent. When appropriate, the individual then relaxes the external sphincter and voiding takes place.

There is a great variation in voiding patterns in the normal population. Normal voiding patterns can range from 4 to 6 hours to every 8 to 12 hours. Persons over the age of 65 may urinate every 3 to 4 hours and awaken to void at least once during the night.

Bladder sensation can change with age. Instead of perceiving the sensation of the bladder filling at about half capacity (as do younger people), many older adults first feel the need to void at, or near, bladder capacity. To an active and mobile person, it can be a considerable inconvenience to locate toilet facilities immediately. To an immobile older adult or an individual with an unstable bladder or painful arthritis, this lack of time between the perception of the need to void and the actual release of urine can result in urinary incontinence.

As can be appreciated above, urinary control relies upon the finely coordinated activities of the smooth muscle tissue of the urethra and bladder, skeletal muscle, voluntary inhibition, and the autonomic nervous system. Loss of control of any or all of these activities can result in urinary incontinence, causing inadequate urinary storage or control.

Figure 2:
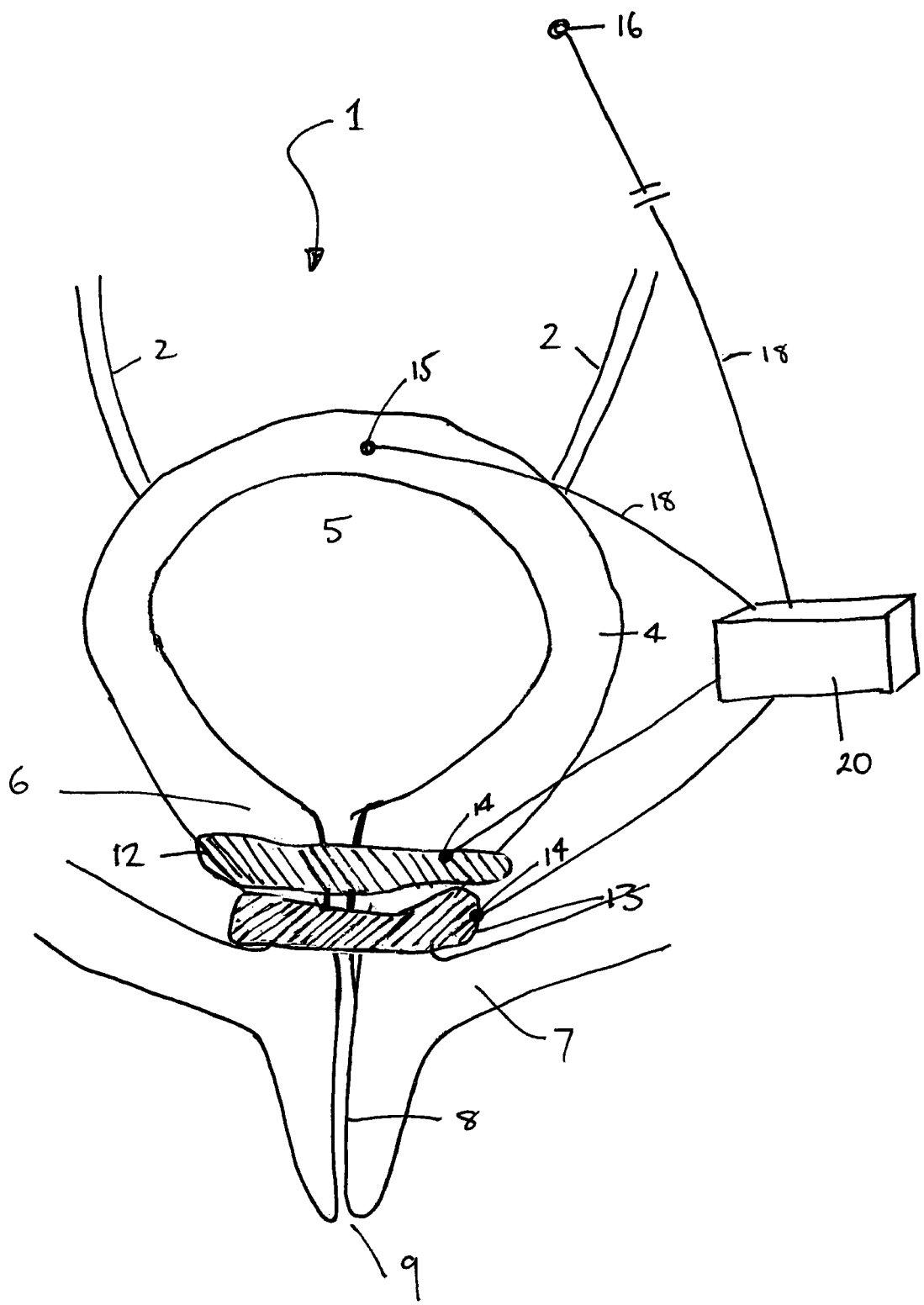
FIG. 2 is a view of the lower urinary tract of a female employing one embodiment of the present invention.

One embodiment of the present invention is shown in relation to FIG. 2 which combines low-frequency stimulation of fatigue resistant smooth muscle for chronic maintenance of continence with higher-frequency stimulation of striated muscle on demand by the user for occasions where abdominal pressure rises.

As in FIG. 1, a lower urinary tract of a female is shown in FIG. 2 with each of the features being similarly numbered. It should be appreciated that the present invention applies equally to a lower urinary tract of a male. An implantable stimulator unit 20 is provided which is connected to a surgically implanted smooth muscle sphincter 12 and a surgically implanted striated muscle sphincter 13 by appropriately positioned stimulating electrodes 14. Each of the surgically implanted sphincters are positioned around the urethra 8 for controlling the flow of urine therethrough.

Sensors 15 and 16 are also connected to the implantable stimulator unit 20 via electrically conducting wires 18 for sensing the volume of urine present in the bladder and the increase in intra-abdominal pressure associated with laughing, sneezing, coughing etc, respectively.

The implantable stimulator unit 20 includes signal processing electronics capable of receiving data from the sensors 15, 16 and/or from an external controller unit. Upon receiving such data, the data is processed by a signal processing unit to provide a predetermined electrical stimulation signal to be applied to the implanted smooth muscle sphincter 12 and/or the striated muscle sphincter 13 via the stimulating electrodes 14. The decision on which sphincter is stimulated and to what degree is decided by the signal processing unit, in accordance with predetermined conditions being met.

The smooth muscle sphincter 12 can be taken from the smooth muscle of the bladder and transplanted about the urethra 8 in the manner as shown. Taking the smooth muscle sphincter from this region allows neurovascular supplies to be preserved with the muscle capable of contracting independently of the rest of the detrusor, whilst having some innervation in common. Alternatively, the muscle may be taken from the venous smooth, anococcygeus smooth muscle, taenia coli, or obtained by resection from the bowel. It is also envisaged that the smooth muscle sphincter 12 can be taken from the dartos smooth muscle from the scrotum or labia, with the blood supply and innervation preserved. Other suitable muscle could also be employed. Equally, the striated muscle sphincter 13 could be formed from the external urethral sphincter or any other suitable muscle.

The muscle taken is typically in the form of a rectangular strip which is arranged to align the muscle fibres in effective orientations around the urethra, thus forming each of the sphincters 12 and 13. The dimensions of the strip of muscle taken may be in the range of 40-80 mm*10-30 mm.

In the embodiment shown in FIG. 2, the system is totally implanted and can function without the presence of an external controller unit.

In this system, sensor 15 detects the amount of urine present in the bladder by sensing the elasticity of the bladder wall. Typically, as the bladder fills with urine, the bladder is elastic and allows room for additional fluid to be accommodated without causing high pressure within the bladder itself. This detection can be performed by monitoring the changes in shape and stretching of the bladder wall via an impedance varying means such as that described in the applicant's co-pending International Patent Application No. PCT/AU03/00653.

Equally, the sensor 15 could monitor the presence of reflex contractions of the detrusor muscle in the bladder. As previously mentioned, when typically 250-300 cc of urine is present in the bladder, the internal pressure within the bladder becomes strong enough to activate stretch receptors in the bladder wall. It is when these stretch receptors send a message to the nervous system that small contractile waves occur in the detrusor muscle causing the internal urethral sphincter to relax to void the bladder. By sensing such contractions, the system can apply the necessary stimulation to the appropriate implanted sphincter to ensure bladder continence and control.

Sensor 16 detects the increase in abdominal pressure resulting from an event such as laughing, coughing, sneezing, lifting or exercising, which typically has resulted in urine emission in patients suffering from incontinence. Typically, in such events, urine emission is caused by the abdominal muscles pushing down on the lower bladder.

With sensor 16 detecting such an event, the system can apply the necessary stimulation to the appropriate sphincter(s) to ensure that unwanted emission is stopped.

Figure 3:
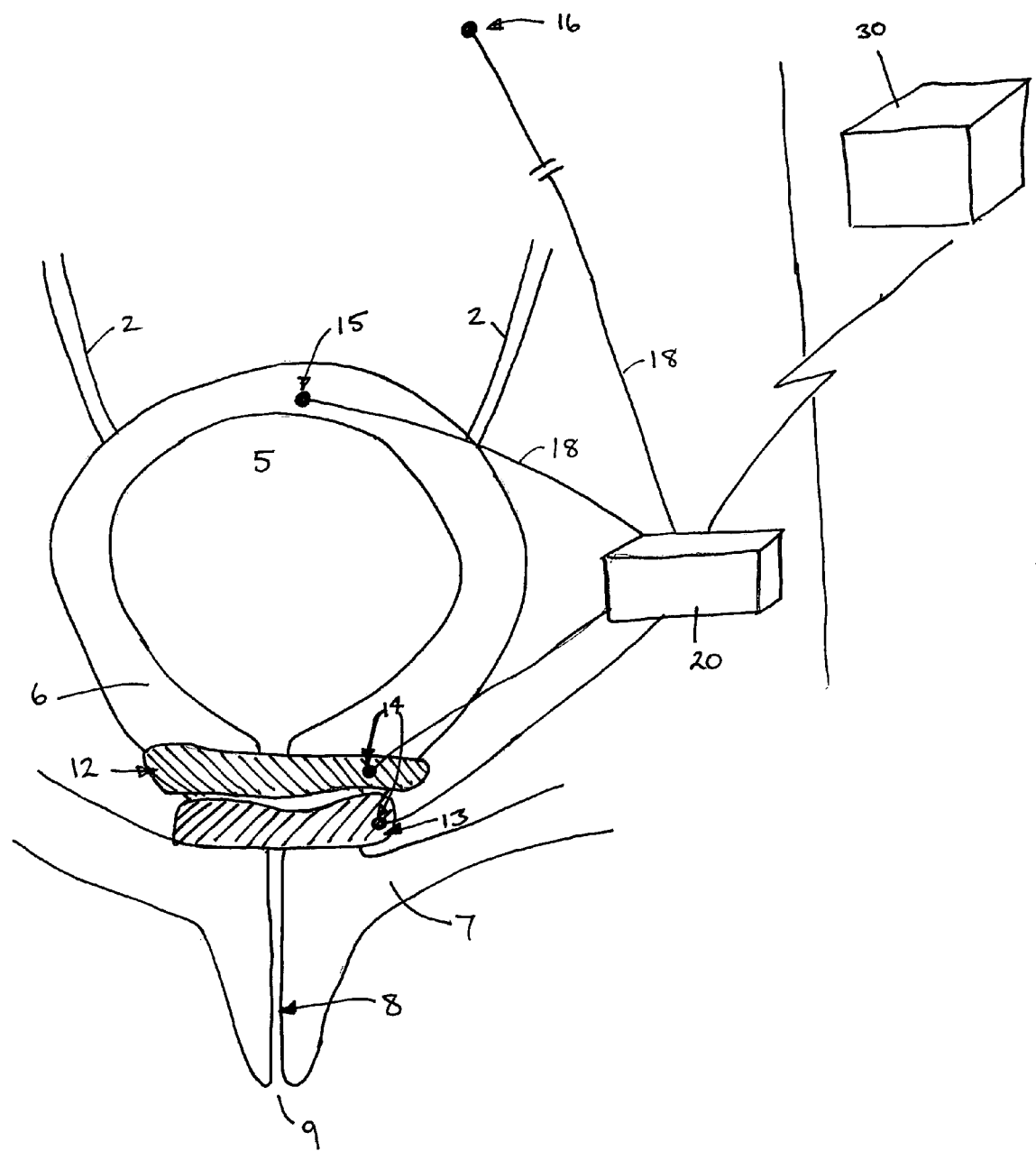
FIG. 3 is a view of the lower urinary tract of a female employing an alternative embodiment of the present invention.

FIG. 3 shows an alternative embodiment of the present invention wherein the implantable stimulator unit 20 is controlled by an external controller 30. In this embodiment, the external controller 30 communicates with the implantable stimulator unit 20 via an appropriate transcutaneous link, such as a radio frequency (RF) signal link. The external controller 30 is a programmable device allowing information to be stored and received from the controller and is preferably a PDA unit having an LCD display and operable controllers.

The external controller 30 includes an RF transmitter/receiver for both generating and transmitting a control signal to the implantable stimulator unit 20 and for receiving data from the implantable stimulator unit 20. In this regard, the patient can indicate that he/she wishes to void the bladder by appropriately indicating so on the external controller, and the external controller then generates and transmits a control signal to the implantable stimulator unit to execute this command. The implantable stimulator unit can also transmit information to the external controller 30 such as bladder capacity and other such information which could then be conveyed to the patient via the external controller. This may be particularly important if the information conveyed is relating to measured bladder capacity as this could allow the patient to regulate their bladder activity by being aware of the amount of urine stored within the bladder.

In use, the systems described in FIGS. 2 and 3 detect both the level of fluid present in the bladder and any increase in intra-abdominal pressure and apply stimulation to the relative sphincter accordingly. In this regard, the stimulator unit 20 provides continuous low-frequency electrical stimulation in the range of 0.25-2.5 Hz via electrode(s) 14 to the smooth muscle sphincter 12 to maintain continence. The volume of fluid present in the bladder is then monitored by way of sensor 15 with the state of the bladder volume being constantly compared to a maximum volume by the stimulator unit 20. Alternatively, the stimulator unit 20 can transmit data to the external controller 30 to provide some form of visual and/or aural indication of bladder volume. In this regard, upon detection of the bladder volume being at a predetermined level, or upon a command from the external controller 30 to evacuate the bladder, stimulation of the smooth muscle sphincter 12 is ceased, thereby allowing voiding of the bladder to occur. Upon cessation of the voiding process, low frequency electrical stimulation to the smooth muscle sphincter 12 is then resumed.

The purpose of the additional striated muscle sphincter 13 is to act independently of the smooth muscle sphincter and to provide relief against stress incontinence due to sudden increases in intra-abdominal pressure which may result from activities such as lifting, sneezing, coughing and the like. In this regard, a pressure sensor 16 is provided in the lower abdomen to detect any sudden increases in intra-abdominal pressure which may cause undue pressure on the bladder cavity. Upon detection of such a condition, high frequency stimulation above 2.5 Hz is applied to the striated muscle sphincter 13 to cause this sphincter to contract and tighten around the urethra 8 to prevent any unwanted voiding of urine from the bladder. Such high frequency stimulation of the striated muscle sphincter 13 occurs only when a condition of high abdominal pressure is detected, otherwise the striated muscle sphincter remains in a relatively relaxed state.

The present invention therefore provides for a system that resembles the natural bladder sphincter system by combining low-frequency stimulation of fatigue-resistant smooth muscle for chronic maintenance of continence with higher frequency stimulation of striated muscle for maintenance of continence when an increase in intra-abdominal pressure is detected.

Whilst the present invention is directed towards providing treatment for incontinence and the specific application of bladder control, it should also be appreciated that the present invention could also be employed to control other bodily organs, such as the bowel or the gastric system. In this regard, transplanted muscle sphincters could be provided to control the function of such organs in much the same way as has been described above in relation to the bladder.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A sphincteric control system for controlling the function of a bodily organ, the sphincteric control system comprising:
 a first implanted sphincter disposed about a portion of the bodily organ;
 a second implanted sphincter disposed about a portion of the bodily organ; and
 a stimulator unit adapted to apply electrical stimulation to each of said first and second implanted sphincters;
 wherein one of said first or second implanted sphincters is made from a smooth muscle and the other of said first or second implanted sphincters is made from a striated muscle.

2. The sphincteric control system of claim 1 wherein the stimulator unit controls the bodily organ by delivering a predetermined electrical stimulation signal to each of the implanted sphincters, causing said sphincters to contract and relax about the bodily organ.

3. The sphincteric control system of claim 2 wherein the predetermined electrical stimulation is in the form of a relatively low frequency stimulation signal when applied to the smooth muscle sphincter.

4. The sphincteric control system of claim 2 wherein the predetermined electrical stimulation is in the form of a relatively high frequency stimulation signal when applied to the striated muscle sphincter.

5. The sphincteric control system of claim 1 wherein the stimulator unit applies the electrical stimulation to each of the implanted sphincters via stimulating electrode elements positioned in or on the implanted sphincters.

6. The sphincteric control system of claim 1 wherein each of the implanted sphincters are positioned around the urethra of a patient for controlling the flow of urine therethrough.

7. The sphincteric control system of claim 6 further comprising one or more sensors for sensing the volume of urine present in the bladder of the patient.

8. The sphincteric control system of claim 6 further comprising one or more sensors for sensing any increase in intra-abdominal pressure of the patient.

9. The sphincteric control system of claim 7 further comprising one or more sensors for sensing any increase in intra-abdominal pressure of the patient.

10. The sphincteric control system of claim 7 wherein the stimulator unit is implantable.

11. The sphincteric control system of claim 10 wherein the stimulator unit includes signal processing electronics capable of receiving data from the sensors and/or from an external controller unit.

12. The sphincteric control system of claim 1 wherein the system is totally implantable.

13. The sphincteric control system of claim 12 wherein the implantable stimulator unit is controllable by an external controller.

14. The sphincteric control system of claim 13 wherein the external controller communicates with the implantable stimulator unit via a transcutaneous link.

15. The sphincteric control system of claim 14 wherein the transcutaneous link is a radio frequency (RF) signal link.

16. The sphincteric control system of claim 13 wherein the external controller is a programmable device.

17. The sphincteric control system of claim 16 wherein the external controller includes an RF transmitter/receiver for both generating and transmitting a control signal to the implantable stimulator unit and for receiving data from the implantable stimulator unit.

18. The sphincteric control system of claim 17 wherein the external controller is operable by the patient or a third person to control the operation of the system.

19. The sphincteric control system of claim 3 wherein the stimulator unit is operable to provide electrical stimulation in the range of 0.25-2.5 Hz to the smooth muscle sphincter.

20. The sphincteric control system of claim 4 wherein the stimulator unit is operable to provide electrical stimulation above 2.5 Hz to the striated muscle sphincter.

21. The sphincteric control system of claim 8 wherein the stimulator unit is implantable.

22. The sphincteric control system of claim 9 wherein the stimulator unit is implantable.

23. A method of controlling the function of a bodily organ comprising:
   implanting a first sphincter about a portion of the bodily organ;
   implanting a second sphincter about a portion of the bodily organ; and applying electrical stimulation to each of said first and second implanted sphincters using a stimulator unit;
   wherein one of said first or second implanted sphincters is made from a smooth muscle and the other of said first or second implanted sphincters is made from a striated muscle.

* * * * *